United States Patent [19]

Grayson et al.

[11] Patent Number: 5,112,995

[45] Date of Patent: May 12, 1992

[54] PREPARATION OF SUBSTITUTED ETHENES

[75] Inventors: James I. Grayson; Graham Heyes, both of Durham City; Arthur Jackson, Washington; Paul E. Rowney, Acklam, all of England

[73] Assignee: Glaxo Group Limited, London, England

[21] Appl. No.: 503,987

[22] Filed: Apr. 4, 1990

[30] Foreign Application Priority Data

Apr. 5, 1989 [GB] United Kingdom ............ 8907700

[51] Int. Cl.$^5$ ............ C07C 319/22; C07C 323/27
[52] U.S. Cl. .................. 549/493; 564/469; 564/485; 564/501
[58] Field of Search ............ 549/495; 564/469, 485, 564/501

[56] References Cited

FOREIGN PATENT DOCUMENTS 523448 12/1985 Spain .
2003781 11/1988 Spain .
2160204B 12/1985 United Kingdom .
90/12002 10/1990 World Int. Prop. O. .

OTHER PUBLICATIONS

*Chemical Abstract* 112(7), Feb. 12, 1990, Abstract No. 54989d.

*Primary Examiner*—Richard L. Raymond
*Attorney, Agent, or Firm*—Bacon & Thomas

[57] ABSTRACT

A potassium salt useful in the production of N-substituted-1-alkylthio-2-nitroethenamines is produced by the reaction of the dipotassium salt of nitrodithioacetic acid with certain straight chain alkylamines, thereby converting only one of the KS-groups to an alkylamine group. The resulting monopotassium salt may be alkylated to produce the required N-substituted-1-alkylthio compound which may be reacted with a suitable amine to produce the histamine $H_2$-antagonist ranitidine.

14 Claims, No Drawings

PREPARATION OF SUBSTITUTED ETHENES

The present invention relates to the preparation of certain substituted ethenes, more specifically certain N-substituted-1-alkylthio-2-nitroethenamines. Such derivatives are useful as intermediates in the manufacture of pharmaceutically active compounds, including particularly the histamine $H_2$-antagonist N-[2-[5-(dimethylamino)methyl-2-furanylmethylthio]ethyl]-N'-methyl-2-nitro-1,1-ethenediamine known as ranitidine.

Spanish Patent Specification No. 523448 describes the preparation of the N-substituted-1-alkylthio-2-nitroethenamine N-methyl-1-methylthio-2-nitroethenamine, by the following reaction sequence:

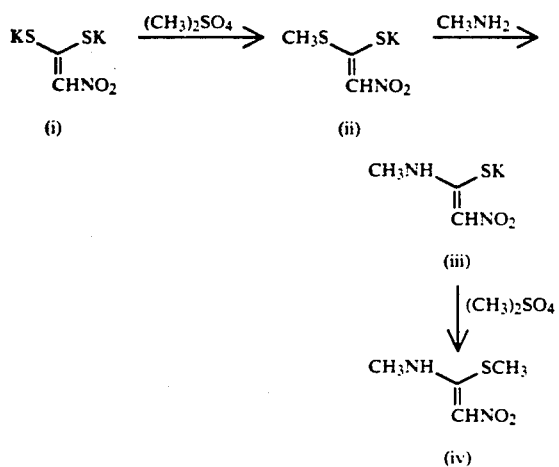

The starting material in the above sequence is the dipotassium salt of nitrodithioacetic acid (1-nitro-2,2-bismercapto-ethylene), and the three stage process involves firstly a methylation by reaction with dimethyl sulphate, secondly the conversion of the resulting $CH_3S$-group into a $CH_3NH-$ group by reaction with methylamine and thirdly a further methylation using a further quantity of dimethyl sulphate.

UK Patent Specification No. 2160204 also describes the preparation of N-methyl-1-alkylthio (e.g. 1-methylthio)-2-nitroethenamines by a process involving alkylation (e.g. methylation) of an intermediate such as (iii) above.

The three stage process described in the Spanish Patent has been found to require careful control at all stages to avoid the production of unwanted reaction products such as the bis(methylthio) derivative and is disadvantageous in requiring a repetition of the dimethyl sulphate reaction due to the toxic nature of that compound.

It is known in the chemical art that, in general, amines do not react with dianions since the lone pair electrons on the amine inhibit reaction with a molecule which is already doubly negatively charged. This inhibition does not apply to dimethyl sulphate. The processing sequence of the Spanish Patent No. 523448 is therefore in accord with current belief in the art.

The present applicant has found surprisingly, however, that certain amines can be made to react directly with the nitrodithioacetate dianion. This has enabled a highly selective two stage process for the production of aminosubstituted thiosubstituted nitroethenes to be developed which uses one processing step less than the Spanish Patent, is robust in that it does not require close control at each process step, does not oversubstitute at all during the amination and provides the desired product in excellent yield.

The present invention provides a method for the production of a potassium salt of formula (I)

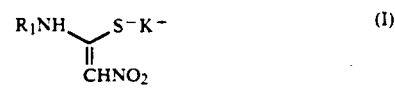

in which $R_1$ represents a straight chain $C_{1-4}$ alkyl group or a substituted straight chain alkyl group containing a heteroatom in the chain which comprises reacting a primary alkylamine selected from $C_{1-4}$ straight chain primary alkylamines and substituted straight chain primary alkylamines containing a heteroatom in the chain with the dipotassium salt of nitrodithioacetic acid.

According to a preferred embodiment of the invention, dipotassium nitrodithioacetate may be reacted with methylamine to give a compound of formula (I) in which $R_1$ is a methyl group. This product has been confirmed by the Applicant by thin layer chromatography to be the same compound as that produced by the second reaction step (reaction with methylamine) of the above-identified Spanish patent and Exemplified therein in Example 2 paragraphs 1 and 2.

Other primary alkylamines within the scope of the present invention are those based on straight chains of, for example, 2 to 4 carbon atoms. In the primary alkylamine chain containing a heteroatom, such heteroatom may, for example, be sulphur the chain being typically

an example of a compound containing such a chain and being within the scope of the present invention being

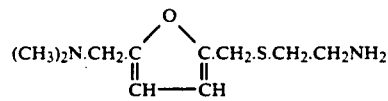

that is, 2-[5-(N,N-dimethylaminomethyl)-2-furanmethylthio] ethylamine. It is understood from the above that the primary alkylamine containing a heteroatom may be substituted, without destroying its essential primary amine character. The product of this last identified amine, on reaction according to the invention with dipotassium nitrodithioacetate to achieve amination of one of the KS-groups, is novel, has the formula

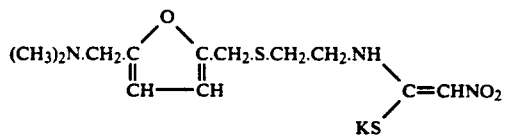

and constitutes a further feature of the invention.

The potassium salt of formula (I) may subsequently be alkylated to give an N-substituted-1-alkylthio-2-nitroethenamine of formula (II)

in which $R_1$ is as defined in formula (I) and $R_2$ represents a $C_{1-4}$ alkyl group, preferably methyl.

The dipotassium salt of nitrodithioacetic acid required as a starting material may be prepared by the method of E Freund, Chem. Ber. 52, 542 (1919) which produces an ethanol-wet cake. Weights given herein are on a 100% basis, the ethanol being treated as solvent.

We prefer to carry out the amination reaction in a polar solvent, for example, water, methanol, ethanol, isopropanol or dimethyl sulphoxide. On costs and ease of handling, water is the preferred solvent. The reaction concentration (water or other solvent to dipotassium salt of nitrodithioacetic acid) can be 20:1 to 1:1 but is preferably 10:1 to 5:1 by weight. All concentrations quoted herein are in parts by weight unless otherwise stated.

For the amination stage good yields can be obtained using an amine:dipotassium salt of nitrodithioacetic acid molar ratio of 0.8:1 to >2:1 but for the best economics a ratio of 1.1:1 is preferred.

The reaction temperature for the amination reaction can be in the range 0° C. to 100° C. but it is preferably between 20° C. and 60° C.

The alkylation reaction to convert the thioamide salt to the thio-alkyl derivative can be carried out in the range 0° C. to 60° C., but it is preferably carried out in the range 10° C. to 40° C. so as to give an acceptable reaction time and avoid side reactions.

Suitable alkylating agents are alkyl halides or sulphates. Particularly convenient agents are dimethyl sulphate, diethyl sulphate, methyl chloride, methyl bromide, and methyl iodide, of which dimethyl sulphate is particularly preferred. Conveniently the alkylation is effected in the presence of a phase transfer agent such as benzyltrimethylammonium chloride.

During the alkylation stage, molar ratios of alkylating agent:dipotassium salt of nitrodithioacetic acid of 1:1 to >4:1 can be used, but optimum yields are obtained using a molar ratio of 2:1 to 2.5:1.

Preferably the potassium salt of formula (I) is reacted in situ with the alkylating agent, and in this case the reaction will in general be carried out in the same solvent as the amination stage.

A preferred process according to the invention comprises reacting dipotassium nitrodithioacetate with methylamine to give the compound of formula (I) in which $R_1$ is a methyl group in situ, followed by methylation using dimethyl sulphate to give N-methyl-1-methylthio-2-nitroethenamine, i.e. the compound of formula (II) in which $R_1$ and $R_2$ both represent methyl groups.

The nitroethenamine product of formula (II) may be recovered by conventional work-up procedures such as filtration or, more preferably, extraction from the reaction mixture using a suitable organic solvent which is, preferably, a substantially water immiscible chlorinated solvent such as methylene chloride, ethylene dichloride or chlorobenzene followed by drying and concentrating of the organic extract. The product obtained from the work-up procedure is desirably recrystallised from a suitable solvent such as propan-2-ol.

According to a further aspect, the invention provides a process for the preparation of ranitidine which comprises reacting an N-substituted-1-alkylthio-2-nitroethenamine of formula (II), prepared as described above, with an appropriate amine.

According to a particular embodiment of this further aspect of the invention, ranitidine may be prepared from 2-[5-(N,N-dimethylaminomethyl)-2-furanmethylthio]ethylamine as the amine, preferably using N-methyl-1-methylthio-2-nitroethenamine as the compound of formula (II). Alternatively ranitidine may be prepared by reacting the compound of formula (II) in which $R_1$ is the 2-[5-(N,N-dimethylaminomethyl)-2-furanmethylthio]ethyl moiety and $R_2$ is an alkyl group (more preferably a methyl group) with methylamine.

In order that the present invention may more readily be understood, certain preparations in accordance therewith will now be described in detail.

EXAMPLE 1

N-methyl-1-methylthio-2-nitroethenamine

Dipotassium nitrodithioacetate (129 g) was dissolved in 560 ml of water. Aqueous methylamine (40% w/w, 52 g) was then added and the solution stirred at 30° C. for 6 hours to allow the formation of 1-(methylamino)-2-nitroethenethiol potassium salt to go to completion.

After cooling to 20° C., benzyltrimethylammonium chloride (8 g) was added to the solution produced as above described followed by dimethyl sulphate (191 g) over about one hour. The evolved methanethiol was removed in a suitable scrubber.

After stirring overnight, the reaction mixture was filtered to remove the precipitated solid which, after recrystallisation from propan-2-ol, gave the title compound having a melting point of 110° C. in a yield of 61 g. This corresponds to a yield of 68.7% based on the dipotassium compound.

EXAMPLE 2

N-Methyl-1-methylthio-2-nitroethenamine

In a preparation otherwise, identical to that described in Example 1 the reaction mixture obtained after stirring overnight was extracted with dichloromethane (3 × 100 ml). After drying with magnesium sulphate the combined organic phases were concentrated and the residue recrystallised from propan-2-ol to yield 76 g of the title compound having a melting point of 110° C. This corresponds to a yield of 85.7% based on the dipotassium compound.

EXAMPLE 3

N-[2-[5-(dimethylamino)methyl-2-furanylmethylthio]-ethyl]-N'-methyl-2-nitro-1,1-ethenediamine A solution of 2-[5-(N,N-dimethylaminomethyl)-2-furanmethylthio]ethylamine (32.1 g) in water (25 ml) was added dropwise over 4 hours to a stirred solution of N-methyl-1-methylthio-2-nitroethenamine (23 g) in water (40 ml) at 50° C. The reaction mixture was heated at 50° C. for a further 2 hours and then heated to 90° C. Methyl isobutyl ketone (150 ml) was added to the solution and the water removed by azeotropic distillation. The solution was cooled at 60° C. and charcoal (1.5 g) added. The mixture was filtered, the charcoal residue washed with methyl isobutyl ketone (50 ml) and the combined filtrate and washings were cooled to 0° C. The title compound having a melting point of 68°-70° C. crystallised in a yield of 39 g and was filtered off.

EXAMPLE 4

1-[[2-[[[5-[(dimethylamino)methyl]-2-furanyl]methyl]-thio]ethyl]amino]-2-nitroethenethiol potassium salt To dipotassium nitrodithioacetate (139 g) dissolved in 560 mls of water was added 2-[5-(N,N-dimethylaminomethyl)-2-furanmethylthio]ethylamine (195 g) over about 45 minutes. The reaction mixture was heated at 40° C. for 2 hours, then at 60° C. for a further two hours and was finally stirred at ambient temperatures overnight to form the title compound t.l.c. silica (1,2-dichloroethane: methanol: acetic acid, 15:5:1) Rf 0.31.

We claim:

1. A method for the production of a potassium salt of formula (I)

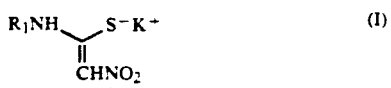

which comprises reacting a primary alkylamine which is $R_1NH_2$, in which $R_1$ represents a straight chain $C_{1-4}$ alkyl group or a substituted straight chain alkyl group containing a heteroatom in the chain, with the dipotassium salt of nitrodithioacetic acid.

2. A method as claimed in claim 1 wherein the amine is methylamine.

3. A method as claimed in claim 1 carried out in water as solvent.

4. A method as claimed in claim 1 wherein the amine is 2-[5-(N,N-dimethylaminomethyl)-2-furanmethylthio]ethylamine.

5. A method as claimed in claim 2 carried out in water as solvent.

6. A method for the production of an N-substituted-1-alkylthio-2-nitroethenamine of formula (II):

in which $R_1$ is a straight chain $C_{1-4}$ alkyl group or a substituted alkyl group containing a heteroatom in the chain and $R_2$ represents a $C_{1-4}$ alkyl group, which comprises preparing a compound of formula (I)

in which $R_1$ is as defined above, by a process wherein a primary alkylamine which is $R_1NH_2$ is reacted with the dipotassium salt of nitrodithioacetic acid, and subsequently reacting the compound of formula (I) with a suitable alkylating agent to produce an N-substituted-1-alkylthio-2-nitroethenamine of formula (II).

7. A method as claimed in claim 6 wherein the reaction with the alkylating agent is carried out on the compound of formula (I) prepared in situ.

8. A method as claimed in claim 6 wherein the alkylating agent is a methylating agent.

9. A method as claimed in claim 8 in which the methylating agent is dimethyl sulphate.

10. A method as claimed in claim 6 wherein the alkylation is conducted in the presence of a phase transfer agent.

11. A method as claimed in claim 6 for the preparation of a compound of formula (II) in which $R_1$ and $R_2$ both represent methyl groups.

12. A process for the preparation of ranitidine which comprises preparing an N-substituted-1-alkylthio-2-nitroethenamine of formula (II):

in which $R_1$ is a methyl group and $R_2$ represents a $C_{1-4}$ alkyl group, which comprises preparing a compound of formula (I)

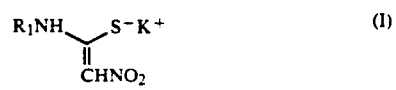

in which $R_1$ is as defined above, by a process wherein a primary alkylamine which is methylamine is reacted with the dipotassium salt of nitrodithioacetic acid, and subsequently reacting the compound of formula (I) with a suitable alkylating agent to produce an N-substituted-1-alkylthio-2-nitroethenamine of formula (II) as defined above, and subsequently reacting the compound of formula (II) with 2-[5-(N,N-dimethylaminomethyl)-2-furanmethylthio]ethylamine to form ranitidine.

13. A process as claimed in claim 12 wherein the compound of formula (II) is N-methyl-1-methylthio-2-nitroethenamine.

14. A process for the preparation of ranitidine which comprises preparing an N-substituted-1-alkylthio-2-nitroethenamine of formula (II):

in which $R_1$ is a 2-[5-(N,N-dimethylaminomethyl)-2-furanmethylthio]ethyl group, and $R_2$ represents a $C_{1-4}$ alkyl group by preparing the compound of formula (I):

in which $R_1$ is as defined above by a process wherein a primary alkylamine which is $R_1NH_2$, wherein $R_1$ is as defined above, is reacted with the dipotassium salt of nitrodithioacetic acid, and subsequently reacting the compound of formula (II) with methylamine.

* * * * *